United States Patent [19]

Furusaki et al.

[11] Patent Number: 5,710,349
[45] Date of Patent: Jan. 20, 1998

[54] PROCESS FOR PRODUCING DIOL COMPOUNDS

[75] Inventors: Shinichi Furusaki; Masaoki Matsuda; Yasunori Miyamoto; Yasushi Shiomi, all of Ube, Japan

[73] Assignee: Ube Industries, Ltd., Ube, Japan

[21] Appl. No.: 448,488

[22] PCT Filed: Oct. 5, 1994

[86] PCT No.: PCT/JP94/01664

§ 371 Date: Jun. 5, 1995

§ 102(e) Date: Jun. 5, 1995

[87] PCT Pub. No.: WO95/10497

PCT Pub. Date: Apr. 20, 1995

[30] Foreign Application Priority Data

Oct. 8, 1993 [JP] Japan .................... 5-253205

[51] Int. Cl.[6] .................................. C07C 29/149
[52] U.S. Cl. .................... 568/864; 502/343; 568/861
[58] Field of Search ..................... 568/864, 861; 502/343

[56] References Cited

U.S. PATENT DOCUMENTS 2,524,892  8/1950  Horlenko et al. .

FOREIGN PATENT DOCUMENTS 45-7287      3/1970   Japan .
B-45-7287    3/1970   Japan .
49-27164     7/1974   Japan .
B-49-27164   7/1974   Japan .
50-160212   12/1975   Japan .
A-50-160212 12/1975   Japan .
52-156192   12/1977   Japan .
A-52-156192 12/1977   Japan .
55-129151   10/1980   Japan .
A-55-129151 10/1980   Japan .
63-141937    6/1988   Japan .
A-63-141937  6/1988   Japan .
3115237      5/1991   Japan .
A-3-115237   5/1991   Japan .

Primary Examiner—Gary Geist
Assistant Examiner—Sreeni Padmanabhan
Attorney, Agent, or Firm—Burgess, Ryan & Wayne

[57] ABSTRACT

In the process of the present invention for producing diol compounds by esterifying a carboxylic acid mixture collected from a reaction product mixture of a liquid phase oxidation of cyclohexane with air and hydrogenate-decomposing the resultant esterification product mixture with hydrogen, the hydrogenate-decomposition is carried out by using a combined catalyst which includes a catalyst (A) including, as principal components, copper oxide and zinc oxide and a catalyst (B) including copper oxide and iron oxide carried on aluminum oxide, does not include chromium, has a high catalytic activity and can be easily separated by filtering, and the combined catalyst is collected from the hydrogenate-decomposition reaction product mixture by filtering it.

6 Claims, 3 Drawing Sheets

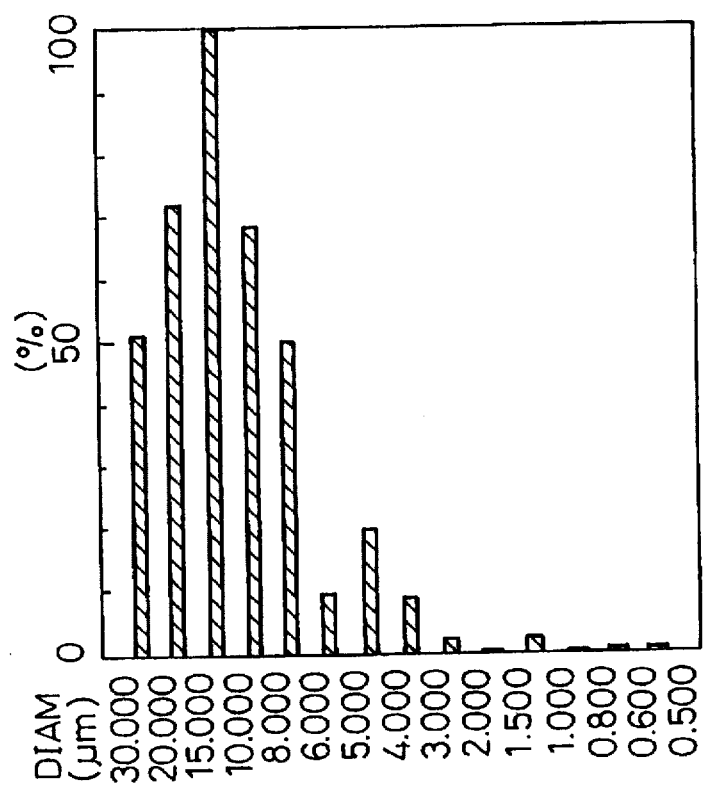
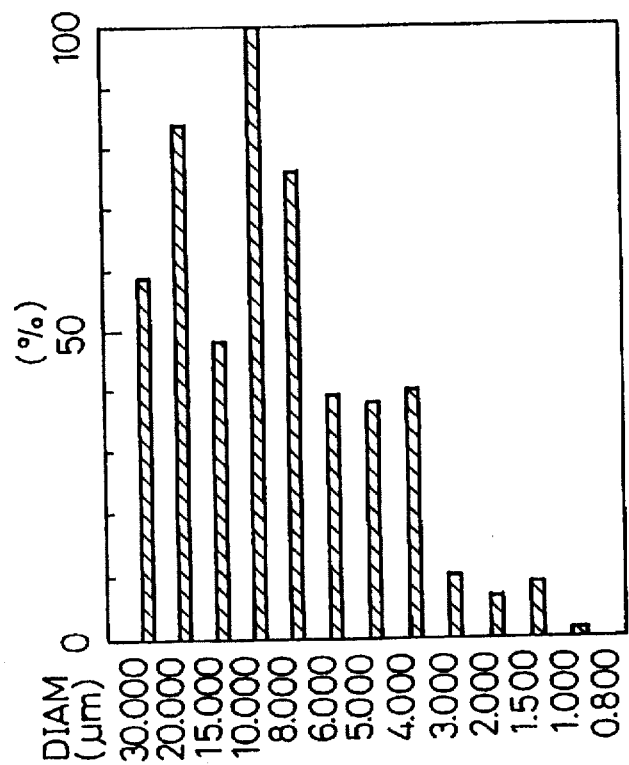

PROCESS FOR PRODUCING DIOL COMPOUNDS

This is the U.S. National Stage Application of PCT/JP94/01664 filed Oct. 5, 1994 now WO95/10497 published Apr. 20, 1995.

TECHNICAL FIELD

The present invention relates to a process for producing diol compounds, for example, 1,6-hexanediol, 1,5-pentanediol and 1,4-butanediol by esterifying a carboxylic acid mixture collected from a reaction product mixture liquid of a liquid phase oxidation of cyclohexane with air, and then hydrogenate-decomposing the resultant esterification product. The diol compounds are useful for polyurethane elastomers, additives for synthetic resins, and intermediates of medicines and agricultural chemicals.

BACKGROUND ART

Cyclohexanol and cyclohexanone, useful as materials for the synthesis of ε-caprolactam, are industrially produced by a liquid phase oxidation of cyclohexane with air. Also, diols, for example, 1,6-hexanediol, are produced by esterifying a carboxylic acid mixture obtained as a by-product of the above-mentioned oxidation reaction with an alcohol, and then hydrogenate-decomposing the resultant esterification product with hydrogen.

In the oxidation reaction of cyclohexane, as a by-product, various carboxylic acids including monobasic acids, for example, caproic acid, valeric acid, butyric acid, propionic acid and acetic acid, and dibasic acids, for example, adipic acid, glutaric acid and succinic acids, are produced. Also, the oxidation product includes various oxyacids, for example, ε-oxycaproic acid and its cyclization product, namely ε-caprolactone. It is known from, for example, "Catalyst", 33, 5, 341 (1991), that the carboxylic acid mixture can be correct-recovered from the oxidation product mixture liquid by extracting with water or rinsing with an aqueous solution of sodium hydroxide or sodium carbonate.

In a process for producing diols, for example 1,6-hexanediol, as disclosed in Japanese Examined Patent Publication (Kokoku) No. 49-27164, a carboxylic acid mixture extracted with water as mentioned above is esterified with an alcohol, particularly a diol, for example, 1,6-hexanediol, and then the resultant esterification product is hydrogenate-decomposed with hydrogen under atmospheric or higher pressure at a reaction temperature of 200° to 350° C., in the presence of a hydrogenation catalyst consisting of a copper-chromium-containing catalyst, and the diols are separated from the reaction product mixture liquid.

In another process as disclosed in Japanese Examined Patent Publication (Kokoku) No. 53-33567, the sodium salt of the carboxylic acid obtained by the above-mentioned alkali-rinsing is neutralized, a carboxylic acid mixture comprising, as principal components, adipic acid and oxycaproic acid is extracted with an organic solvent, for example, methylisobutylketone, the resultant extract is esterified with a diol compound, for example, 1,6-hexanediol, and then the esterification product is hydrogenate-decomposed with hydrogen under a pressure of 200 to 300 kg/cm² at a reaction temperature of 240° to 290° C., to produce diol compounds.

In these processes in which the carboxylic acid mixture separated from the reaction product mixture liquid of the liquid phase oxidation of cyclohexane with air is esterified, and the resultant esterification product is hydrogenate-decomposed with hydrogen to produce diol compounds, for example, 1,6-hexanediol, alcohols including, as principal components, diols which are the reaction product, are used as an esterifying agent. This is due to the fact that the esterification of the carboxylic acid mixture without using a catalyst needs to be effected at a high reaction temperature of 200° C. or more, and thus when a monohydric alcohol, for example, methyl alcohol or ethyl alcohol is used, the reaction must be carried out under a high pressure, and the high temperature high pressure process requires expensive reaction equipment, is significantly dangerous and thus is not industrially preferable. Also, to effect the esterification at a reduced temperature, it has been attempted to use a catalyst such as sulfuric acid. This attempt, however, causes a problem for the separation of the catalyst and the treatment of the waste liquid to occur, and thus is not industrially preferred.

For the above-mentioned reasons, diol compounds, for example, 1,6-hexanediol which have a boiling point significantly higher than that of lower monohydric alcohols and can effect the esterification under the ambient atmospheric pressure without using catalyst, are preferably used as esterifying agents. Particularly, a hydrogenate-decomposition reaction product mixture liquid containing 50% or more of diol compounds, for example, 1,6-hexanediol is more preferably used as the esterifying agent, because the diols per se are target products and the separation step which is necessary when the esterification is carried out by using another alcohol compound becomes unnecessary.

In the process for producing diol compounds, for example 1,6-hexanediol, by esterifying a carboxylic acid mixture separated from the reaction product mixture liquid of the liquid phase air oxidation of cyclohexane, and then hydrogenate-decomposing the esterification product with hydrogen, a copper-chromium-containing catalyst is commonly employed as a hydrogenation catalyst.

This is due to the fact that where diol compounds, for example 1,6-hexanediol, are used as an esterifying agent, the diol compounds react with dibasic acids, for example, adipic acid, to produce polyesters having a high molecular weight, the resultant polyesters must be hydrogenate-decomposed at a high reaction temperature of 250° C. or more, and thus the catalyst for the hydrogenate-decomposition reaction is required to exhibit a high activity at a high temperature reaction. Further, since the reaction product mixture liquid obtained by the hydrogenate-decomposition of the carboxylic acid esters has a high viscosity, and thus the separation of the catalyst from the reaction product mixture liquid by filtering is not easy, the catalyst is required to exhibit a high filter-separability.

However, the conventional copper-chromium-containing catalyst contains chromium, which is harmful, and thus when this catalyst is used, specific dust-preventing means are necessary while handling the catalyst. Also, the conventional catalyst is disadvantageous in that specific equipment is necessary for the treatment of discharged water and wasted liquid. Especially, where the reaction is carried out in a liquid phase suspension state, since the catalyst partially dissolves in the reaction liquid, a difficult problem occurs for the treatment of a residue in a distillation column after the diol compounds, for example, 1,6-hexanediol, are collected from the reaction product mixture liquid by distillation.

Accordingly, various chromium-free catalysts have been attempted for the process for producing alcohol compounds by hydrogenate-decomposing carboxylic acid esters with hydrogen. However, these conventional catalysts are not industrially satisfactory for the production of the diol compounds, for example, 1,6-hexanediol.

For example, Japanese Unexamined Patent Publication (Kokai) No. 63-141937 discloses a process for producing lauryl alcohol from methyl laurate by using a catalyst consisting of copper oxide and zinc oxide. Where this catalyst is applied to the production of 1,6-hexanediol, however, this catalyst is disadvantageous in that the filter-separability of the catalyst is very poor, whereas the activity of the catalyst is higher than that of the conventional copper chromium-containing catalyst.

Also, Japanese Examined Patent Publication (Kokoku) No. 58-50775 discloses a process for producing alcohols from corresponding methyl esters of coconut oil fatty acids by using a catalyst comprising copper oxide and iron oxide carried on aluminum oxide. However, when this catalyst is applied to the production of 1,6-hexanediol, this catalyst exhibits a significantly lower activity than that of the conventional copper-chromium-containing catalyst, whereas the filter-separability of this catalyst is similar to that of the conventional copper-chromium-containing catalyst.

DISCLOSURE OF THE INVENTION

An object of the present invention is to provide a process for producing diol compounds at a high industrial efficiency by esterifying a carboxylic acid mixture collected from a reaction product mixture liquid of a liquid phase oxidation of cyclohexane with air and then hydrogenate-decomposing the resultant esterification product with hydrogen by using a hydrogenating catalyst which has an excellent activity, can be easily separated by filtering, and is free from harmful chromium.

The inventors of the present invention conducted extensive research on the conventional copper-containing catalyst free from chromium, to attain the above-mentioned object, and as a result it was discovered that when the hydrogenate-decomposition reaction is carried out in the presence of two or more conventional copper-containing catalysts free from chromium and combined together, surprisingly, the combined catalyst exhibit a significantly enhanced catalytic activity and can be very easily filter-separated from the reaction product mixture liquid. The present invention was completed based on this discovery.

Namely, the process of the present invention for producing diol compounds comprises the steps of; esterifying a carboxylic acid mixture collected from a reaction product mixture liquid obtained by a liquid phase oxidation reaction of cyclohexane with air, and hydrogenate-decomposing the resultant esterification product with hydrogen, and is characterized in that the hydrogenate-decomposition of the esterification product with hydrogen is carried out in the presence of a combined catalyst comprising a catalyst (which will be referred to as a catalyst (A) hereinafter) comprising, as principal components, copper oxide and zinc oxide and a catalyst (which will be referred to as a catalyst (B) hereinafter) comprising copper oxide and iron oxide carried on aluminum oxide.

The combined catalyst means a catalyst consisting of the catalyst (A) and the catalyst (B) combined or mixed together.

In the process of the present invention, the combined catalyst can be separated from the hydrogenate-decomposition reaction product mixture liquid by filtering, at high efficiency.

BRIEF DESCRIPTION OF THE DRAWINGS

FIG. 1A is a graph showing a distribution of particle size of the combined catalyst (catalyst (A)/catalyst (B) ratio=1/1) disclosed in Example 5, before the reaction;

FIG. 1B is a graph showing a distribution of particle size of the combined catalyst (catalyst (A)/catalyst (B) ratio=1/1) disclosed in Example 5, after the reaction;

BEST MODE OF CARRYING OUT THE INVENTION

Figure 2A:
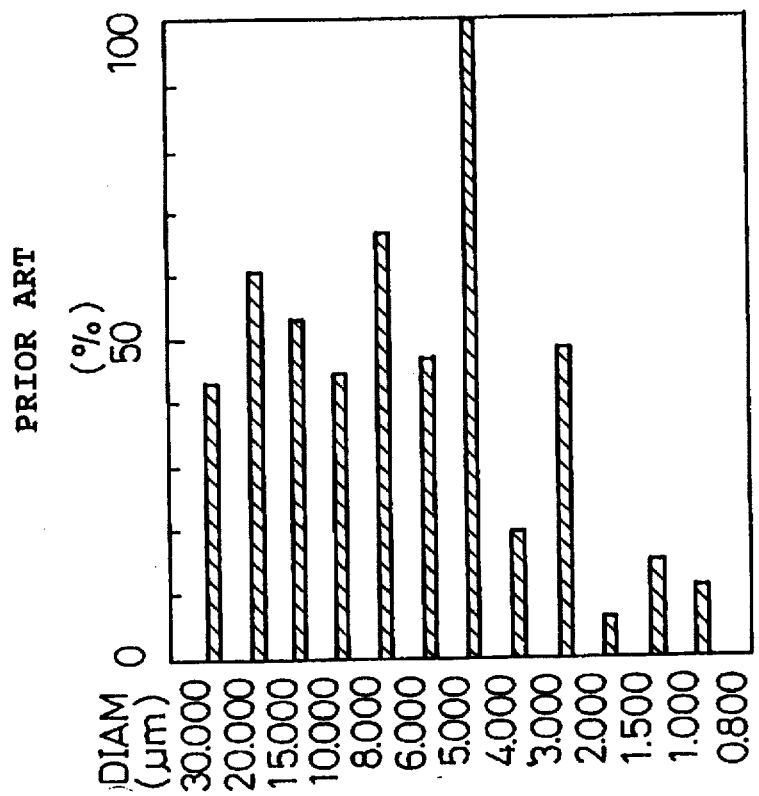
FIG. 2A is a graph showing the distribution of particle size of catalyst (A) described in Comparative Example 3, before the reaction.

The process of the present invention will be explained in detail below.

The carboxylic acid mixture usable for the present invention is collected and recovered from an oxidation reaction product mixture liquid obtained in the production of cyclohexanol and cyclohexanone by a liquid phase oxidation of cyclohexane with air, by a water extraction or an alkali rinsing.

For example, as disclosed in Japanese Examined Patent Publication (Kokoku) No. 49-27164, a carboxylic acid mixture which substantially does not contain cyclohexanol, cyclohexane and monobasic acid can be recovered from the oxidation reaction product mixture liquid by separating an aqueous phase fraction comprising, as principal components, mono-basic acids, for example, caproic acid, valetic acid and butyric acid, dibasic acids, for example, adipic acid, glutaric acid and succinic acid and oxyacids, for example, oxycaproic acid, from the oxidation reaction product mixture liquid by a water extraction, and then concentrating the aqueous phase fraction.

Also, as disclosed in Japanese Examined Patent Publication (Kokoku) No. 53-33567, a carboxylic acid mixture comprising, as principal components, dibasic acids, for example, adipic acid, glutaric acid and succinic acid and oxyacids, for example, oxycaproic acid, can be recovered by rinsing the above-mentioned cyclohexanone-oxidation reaction product mixture liquid with an aqueous sodium hydroxide solution, neutralizing the rinsed liquid with a diluted sulfuric acid, extracting the neutralized liquid with methylisobutyl-ketone and then concentrating the extract.

The esterification product usable for the present invention can be easily prepared by esterifying the carboxylic acid mixture separated and recovered by the above-mentioned method and comprising the dibasic acids, for example, adipic acid, glutaric acid and succinic acid and the oxyacids, for example, oxycaproic acid, with an alcohol to produce esters corresponding to the alcohol. The alcohol usable for the present invention can be selected from monohydric alcohols, for example, methyl alcohol, ethyl alcohol, propyl alcohol, and butyl alcohol, and diols, for example, 1,4-butanediol, 1,5-pentane-diol and 1,6-hexanediol. In this step, to carry out the esterification under the ambient atmospheric pressure without using the catalyst, it is necessary to use an alcohol having a very high boiling temperature, unlike the lower alcohols. 1,6-hexanediol is preferably used, more preferably a hydrogenate-decomposition reaction product mixture liquid derived from the esterification product and containing 50% or more of 1,6-hexanediol, is employed.

The alcohol for the esterification reaction is used in an amount of 1.2 to 1.5 times, in terms of hydroxyl group equivalent of the alcohol, the acid value of the carboxylic acid mixture used as a starting material. If this proportion is less than 1.2 times, the esterification reaction rate becomes very low, so that the esterification cannot be completed, and thus the resultant esterification reaction product mixture exhibits too high an acid value and becomes undesirable as a material for the hydrogenate-decomposition reaction. When the esterification product has an acid value of 5 mgKOH/g or more, the hydrogenating catalyst is very significantly dissolved in the mixture by the action of acidic substances included in the mixture, and thus exhibits a reduced activity. Also, if the proportion is more than 1.5 times, while the reaction is not affected, the total amount of the reaction mixture liquid to be treated becomes large and a large treatment apparatus becomes necessary, and thus a large amount of energy becomes necessary to recover the target diol compound.

With respect to the conditions for the esterification reaction, there is no limitation other than the above-mentioned items. Usually, the esterification is carried out preferably at a reaction temperature of 200° to 250° C. to such an extent that the acid value of the reaction mixture liquid becomes 5 mgKOH/g or less, more preferably 2 mgKOH/g or less. Since the esterification reaction is an equilibrium reaction, the reaction can be rapidly completed by removing a by-product consisting of water by vaporization accompanied with an inert gas, for example, nitrogen gas.

In the process of the present invention, the hydrogenate-decomposition reaction is carried out by hydrogenating and decomposing the esterification product produced by the above-mentioned procedures with hydrogen.

Usually, the hydrogenate-decomposition reaction is carried out preferably at a temperature of 250° to 300° C., more preferably 270° to 300° C. under a hydrogen pressure, at the above-mentioned temperature, of 200 to 300 kg/cm$^2$, more preferably 250 to 300 kg/cm$^2$. If the reaction temperature is higher than 300° C., the by-product consisting of water is produced in an undesirably large amount, and if the hydrogen pressure is higher than 300 kg/cm$^2$, the safety of the reaction apparatus must be considered, and thus these conditions are not preferable.

In the process of the present invention, the hydrogenate-decomposing step of the above-mentioned esterification product with hydrogen is carried out in the presence of a combined catalyst comprising a catalyst (A) comprising, as principal components, copper oxide and zinc oxide and a catalyst (B) comprising copper oxide and iron oxide carried on a carrier consisting of aluminum oxide.

The catalyst (A) usable for the hydrogenate-decomposition reaction of the process of the present invention may be selected from conventional copper-zinc-containing catalysts which are practically used as methyl alcohol-synthesis catalysts, cyclohexanol-dehydrogenating catalysts, low temperature CO-conversion catalysts and gas-refining catalysts for removing hydrogen sulfide or carbon monoxide, and commercially available. These conventional catalysts comprise, as principal components, copper oxide and zinc oxide, and optionally a carrier consisting of, for example, alumina or clay and a binder.

When the catalyst (A) is supplied in the form of a shaped article, the shaped catalyst (A) is usually pulverized and then fed to the process of the present invention. When the catalyst (A) is supplied in the form of a powder, it can be used in the supplied powder form per se for the process of the present invention. In either case, the catalyst (A) powder is preferably one passed through a 200 mesh sieve, and has an average particle size of 1 to 50 µm, more preferably 2 to 20 µm.

The preferable catalyst (A) usable for the process of the present invention is prepared by pulverizing a conventional copper oxide and zinc oxide-containing catalyst, for example, a gas-refining catalyst comprising 40% of CuO, 40% of ZnO and 20% of Al$_2$O$_3$, in the form of pellets and available under the trademark of R3-12, from BASF, a low temperature CO-conversion catalyst comprising 30% of CuO, 60% of ZnO and 10% of clay, in the form of pellets and available under the trademark of G-66G from Nissan Gardler, and sifting the resultant powder through a 200 mesh sieve.

The catalyst (B) usable for the process of the present invention may be selected from conventional catalysts prepared in accordance with the methods disclosed in Japanese Examined Patent Publication (Kokoku) Nos. 45-7287 and 58-50775 and Japanese Unexamined Patent Publication (Kokai) No. 52-156192, and comprising copper oxide and iron oxide carried on a carrier consisting of aluminum oxide. Preferably, the catalyst (B) has an average particle size of 5 to 15 µm. The above-mentioned catalyst contains copper as an active component and can be easily separated by filtering and therefore is particularly appropriate to the present invention.

In the preparation of the combined catalyst usable for the process of the present invention of mixing the catalyst (A) with the catalyst (B), if the content of the catalyst (A) is too high, while the resultant combined catalyst exhibits a high catalytic activity, it becomes difficult to separate the combined catalyst by filtering. If the content of the catalyst (B) is too high, separation of the resultant combined catalyst by filtering is easy, but the catalytic activity of the resultant combined catalyst is reduced. Therefore, the mixing ratio by weight of the catalyst (A) to the catalyst (B) is preferably 1:0.5 to 1:10, more preferably 1:0.5 to 1:8, still more preferably 1:1 to 1:5.

The reason why the combined catalyst exhibits higher catalytic activity and filter-separability than those of each of the catalyst (A) and the catalyst (B) is not yet completely clear. However, the reason is supposed to be, for example, as follows.

In the catalyst (A), copper oxide is fully dispersed by the action of zinc oxide, and thus a portion of copper component is easily dissolved in the reaction mixture liquid. Therefore, when the copper component is reduced by hydrogen during the hydrogenate-decomposition reaction, the resultant copper metal, which serves as a catalytic active component, has a very small particle size. As a result, the resultant catalyst exhibits an enhanced catalytic activity and becomes difficult to separate by filtering.

On other hand, the catalyst (B) has an enhanced filter-separability due to the presence of iron oxide and aluminum oxide. However, the copper oxide in the catalyst (B) exhibits a lower dispersibility than that in the catalyst (A), and thus the catalyst (B) exhibits a reduced catalytic activity.

Figure 2B:
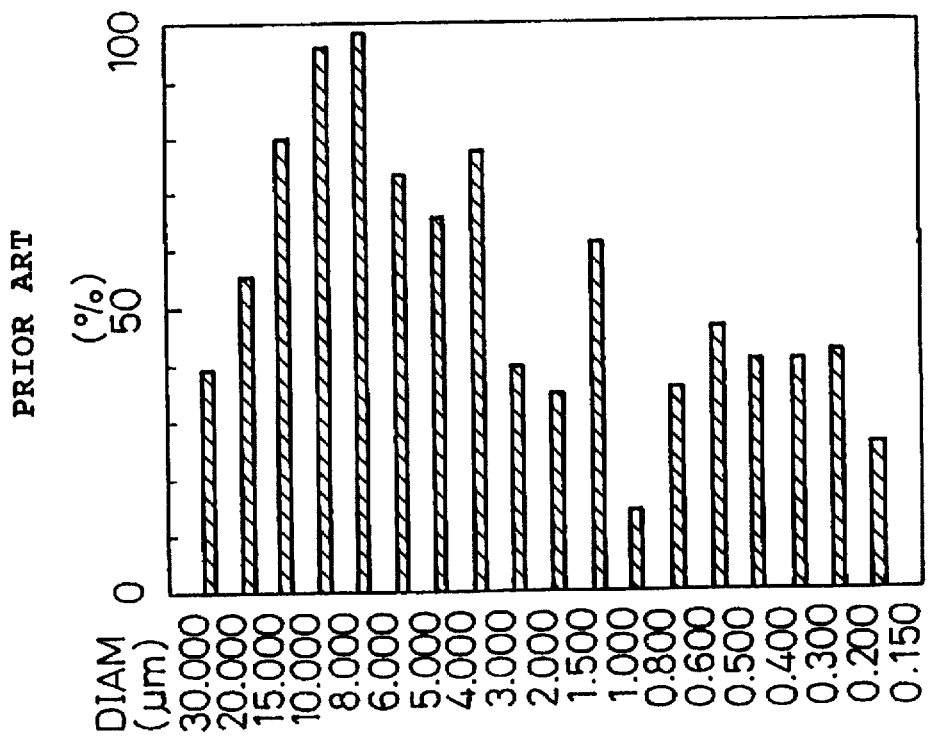
FIG. 2B is a graph showing the distribution of particle size of catalyst (A) described in Comparative Example 3, after the reaction.
Figure 3B:
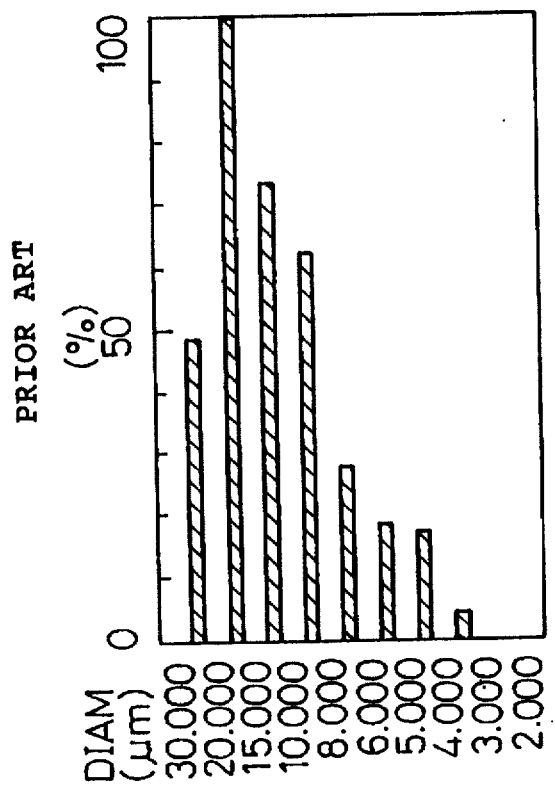
FIG. 3B is graph showing the distribution of particle size of catalyst (B) described in Comparative Example 2, after the reaction.
Figure 3A:
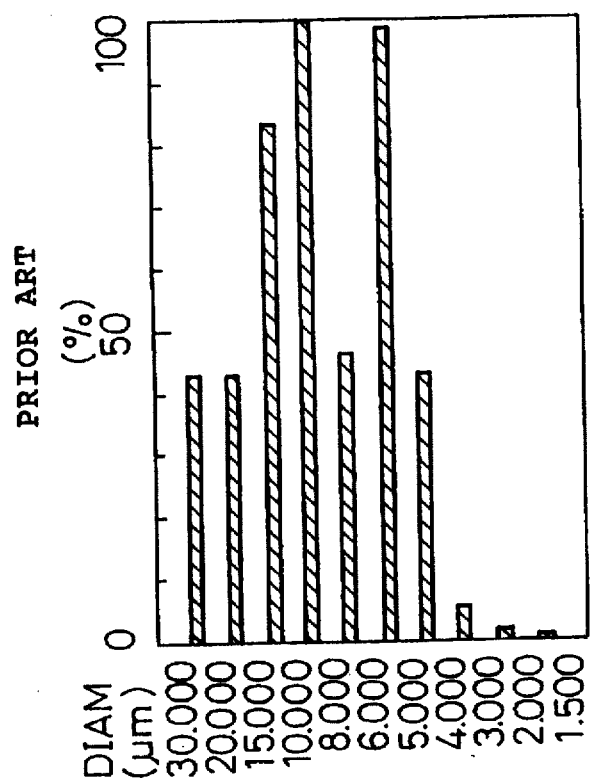
FIG. 3A is a graph showing the distribution of particle size of catalyst (B) described in Comparative Example 2, before the reaction.

Nevertheless, when the catalyst (A) and the catalyst (B) are used in combination thereof, it is assumed that the copper component in the catalyst (A) is dissolved in the reaction mixture liquid and then precipitates on the copper component in the catalyst (B), which is present together with the catalyst (A) and has a high filter-separability, and thereby the combined catalyst exhibits an enhanced catalytic activity and can be easily removed from the reaction mixture liquid by filtering. This phenomenon is proved from the fact that as indicated in FIGS. 1A to 3B, the particle size of the combined catalyst after the reaction is larger than that before the reaction. Accordingly, it is clear that the combined catalyst serves as a new catalyst having catalytic properties different from those of either the catalyst (A) or the catalyst (B).

In the process of the present invention, the hydrogenate-decomposing step can be carried out by using a reaction apparatus having a conventional liquid phase suspension bed.

Namely, the hydrogenate-decomposing step can be carried out by a batchwise reaction method in which the starting material consisting of the esterification product and the combined catalyst are charged into a pressure-resistive reactor and the charged mixture is heated at a reaction temperature under pressure of a hydrogen gas, while stirring the mixture. Otherwise, the combined catalyst is suspended in the esterification product, and the resultant suspension is preheated under pressure of the hydrogen gas, and then subjected to a continuous reaction procedure by introducing the suspension into a lower portion of a reactor.

The combined catalyst is employed preferably in an amount of 0.1 to 3.0% by weight, more preferably 0.3 to 1.5% by weight, based on the weight of the esterification product.

After the hydrogenate-decomposition reaction is completed, the combined catalyst is separated and recovered from the reaction mixture liquid by filtering.

In the process of the present invention, the above-mentioned specific combined catalyst is used and thus can be easily filtered by using a conventional filtering device, for example, a filter-type filtering device.

The target diol compounds, for example, 1,6-hexanediol is easily collected from a filtrate obtained from the above-mentioned filtering procedure, by distilling the filtrate in a reduced pressure distilling apparatus. By the above-mentioned procedures, the target diol compounds, for example, 1,6-hexanediol, 1,5-pentanediol and 1,4-butanediol can be obtained.

EXAMPLES

The process of the present invention will be further explained by way of specific examples.

In the examples and comparative examples, a carboxylic acid mixture prepared by extracting a reaction product mixture liquid of a liquid phase air oxidation of cyclohexane, with water, in accordance with the method disclosed in Japanese Examined Patent Publication (Kokoku) No. 49-27163, was used. The extracted carboxylic acid mixture contained 26.8% by weight of adipic acid, 31.9% by weight of oxycaproic acid, 6.1% by weight of glutaric acid and 1.2% by weight of succinic acid.

In the preparation of an esterification product, 1000 kg of a corresponding carboxylic acid mixture was esterified with 850 kg of a hydrogenate-decomposition product mixture liquid containing 50% or more of 1,6-hexanediol. The resultant esterification product contained 3.1% by weight of 1,6-hexanediol, 1.1% by weight of 1,5-pentanediol and 0.06% by weight of 1,4-butanediol and exhibited an acid value (AV) of 0.8 mgKOH/g and a saponification value (SV) of 343 mgKOH/g.

The above-mentioned hydrogenate-decomposition product mixture liquid was prepared in accordance with the method as disclosed in Example 1 of Japanese Unexamined Patent Publication (Kokai) No. 3-115237, and contained 61.6% by weight of 1,6-hexanediol, 8.5% by weight of 1,5-pentanediol and 0.8% by weight of 1,4-butanediol.

Example 1

A catalyst (A) was prepared by pulverizing a gas-refining catalyst commercially available under the trademark of R3-12, from BASF, in the form of pellets and comprising 40% of CuO, 40% of ZnO and 20% of $Al_2O_3$, sifting the pulverized catalyst particles through a 200 mesh sieve. The resultant catalyst particles passed through the 200 mesh sieve had an average size of 8.3 µm before reaction. A catalyst (B) was prepared in accordance with the method disclosed in Example 1 of Japanese Unexamined Patent Publication (Kokai) No. 58-50775. The resultant catalyst comprised 30% of CuO, 30% of $Fe_2O_3$ and 40% of $Al_2O_3$ and in the form of particles having an average size of 9.7 µm before reaction.

The above-mentioned esterification product of the carboxylic acid mixture in an amount of 350 g and 3.5 g of a combined catalyst consisting of the catalyst (A) and the catalyst (B) in the weight ratio indicated in Table 1 were placed in a stainless steel-made autoclave with a capacity of 500 ml, hydrogen gas was blown into the autoclave under pressure, and the reaction mixture was heated at a reaction temperature of 280° C. under a hydrogen gas pressure of 280 kg/cm² for 5 hours, while stirring the mixture, to hydrogenate-decompose the esterification product.

After the reaction was completed, 350 ml of the resultant reaction product mixture liquid was fed into a pressure filtering device having a capacity of 500 ml, equipped with a 10 µm membrane filter and heated at a temperature of 55° C., and filtered under pressure of 1.0 kg/cm² applied by a nitrogen gas. The filtering time of the mixture liquid was determined by measuring, after a first fraction of the mixture liquid in an amount of 50 ml passed through the filter, the time necessary to filter the following fraction, in an amount of 50 ml, through the filter, by using a stopwatch.

The diol compounds, for example, 1,6-hexanediol, produced by the hydrogenate-decomposition reaction were identified by analyzing the filtrate obtained from the above-mentioned filtering procedure by a gas-chromatography. Also, the saponification values (SV, mgKOH/g) of the esterification product of the carboxylic acid mixture used as a material, and the resultant reaction product mixture liquid were determined by a titration method, and a SV conversion was calculated in accordance with the following equation:

$$SV\ conversion\ (\%) = \frac{(SV\ before\ reaction) - (SV\ after\ reaction)}{SV\ before\ reaction} \times 100$$

The particle size of the combined catalyst was determined, after the combined catalyst filter-separated by the above-mentioned filtering procedure was rinsed with a small amount of methyl alcohol and then dried, by dispersing the dried combined catalyst in ethyl alcohol and by measuring the particle size by using a centrifugal sedimentation type particle size distribution tester which is available under the trademark of SA-CA3 from Shimazu Seisakusho.

The analysis results are shown in Table 1.

Comparative Examples 1 and 2

In each of Comparative Examples 1 and 2, the same process and analysis as in Example 1 were carried out except that the combined catalyst used in Example 1 was replaced by the catalyst (A) or (B) alone.

The analysis results are shown in Table 1.

Examples 2 to 6

In each of Examples 2 to 6, the same process and analysis as in Example 1 were carried out except that a catalyst (A) was prepared by pulverizing a low temperature CO conversion catalyst which was available under the trademark of G-66G from Nissan Gardler Co. in the form of pellets, and comprising 30% of CuO, 60% of ZnO and 10% of clay, and sifting the pulverized particles through a 200 mesh sieve, the resultant catalyst (A) particles had an average size of 6.7 μm before the reaction, and in the preparation of a combined catalyst, the above-mentioned catalyst (A) was mixed with the catalyst (B) in the mixing weight ratio as indicated in Table 1.

The analysis results are shown in Table 1.

Comparative Example 3

The same process and analysis as in Example 2 were carried out except that the combined catalyst was replaced by the catalyst (A) alone.

The analysis results are shown in Table 1.

TABLE 1

| Item Example No. | | Combined catalyst (mixing weight ratio) | | Analysis results of hydrogenate-decomposition product | | | | | | Average particle size of combined catalyst after reaction (μm) |
|---|---|---|---|---|---|---|---|---|---|---|
| | | Catalyst (A) | Catalyst (B) | SV after reaction (mgKOH/g) | SV conversion (%) | Content of 1,6-hexanediol (wt %) | Content of 1,5-pentanediol (wt %) | Content of 1,4-butanediol (wt 5%) | Filtering time (sec) | |
| Example 1 | | 1 | 1 | 18.4 | 94.6 | 53.8 | 9.0 | 0.8 | 41 | 10.7 |
| Comparative | 1 | 1 | 0 | 11.4 | 96.7 | 59.7 | 9.8 | 0.9 | 156 | 4.5 |
| Example | 2 | 0 | 1 | 86.0 | 74.9 | 39.4 | 7.4 | 0.6 | 23 | 13.7 |
| Example | 2 | 1 | 8 | 53.9 | 84.3 | 47.1 | 8.2 | 0.7 | 24 | 13.5 |
| | 3 | 1 | 4 | 34.7 | 89.9 | 52.5 | 8.9 | 0.7 | 26 | 13.3 |
| | 4 | 1 | 2 | 24.0 | 93.0 | 56.1 | 9.1 | 0.8 | 28 | 12.6 |
| | 5 | 1 | 1 | 19.1 | 94.4 | 56.1 | 9.3 | 0.8 | 31 | 12.3 |
| | 6 | 1 | 0.5 | 15.1 | 95.6 | 57.7 | 9.5 | 0.8 | 43 | 11.9 |
| Comparative Example 3 | | 1 | 0 | 11.7 | 96.6 | 58.7 | 9.7 | 0.8 | 273 | 3.7 |

INDUSTRIAL APPLICABILITY

Surprisingly, the problems of the conventional catalysts relating to the catalytic activity and filter-separability thereof can be entirely solved by the process of the present invention. Namely, in the process of the present invention, diol compounds including 1,6-hexanediol can be easily produced by hydrogenate-decomposing, with hydrogen, an esterification product of a carboxylic acid mixture collected from a reaction product mixture liquid of an oxidation of cyclohexane, in the presence of a specific catalyst which is free from chromium, has an excellent catalytic activity and can be easily separated by filtering. The target compounds and the catalyst can be easily separated from each other by filtering.

We claim:

1. A process for producing diol compounds comprising the steps of;

esterifying a carboxylic acid mixture collected from a reaction product mixture liquid obtained by a liquid phase oxidation reaction of cyclohexane with air, with an alcohol, and hydrogenate-decomposing the resultant esterification product with hydrogen, wherein the hydrogenate-decomposition of the esterification product with hydrogen is carried out in the presence of a combined catalyst comprising:

a catalyst (A) comprising, as principal components, copper oxide and zinc oxide in the form of particles passed through a 200 mesh sieve and having an average size of 1 to 50 μm, and a catalyst (B) comprising copper oxide and iron oxide carried on aluminum oxide in the form of particles having an average size of 5 to 15 μm, the catalyst (A) and the catalyst (B) are present in a weight ratio of 1:0.5 to 1:10.

2. The process as claimed in claim 1, wherein the combined catalyst is recovered from the hydrogenate-decomposition reaction product mixture by filtering.

3. The process as claimed in claim 1, wherein the carboxylic acid mixture comprises, as principal components, adipic acid, glutaric acid, succinic acid and caproic acid.

4. The process as claimed in claim 1, wherein the esterification of the carboxylic acid mixture is carried out by using an esterifying agent selected from the group consisting of methyl alcohol, ethyl alcohol, propyl alcohol, butyl alcohol, 1,4-butanediol, 1,5-pentanediol, and 1,6-hexanediol.

5. The process as claimed in claim 1, wherein the hydrogenate-decomposition reaction is carried out at a temperature of 250° to 300° C. under a hydrogen pressure of 200 to 300 kg/cm$^2$.

6. The process as claimed in claim 1, wherein the combined catalyst is employed in an amount of 0.1 to 3.0% based on the weight of the esterification reaction product mixture prepared from the carboxylic acid mixture.

* * * * *